US009468524B2

(12) United States Patent
Caffey et al.

(10) Patent No.: US 9,468,524 B2
(45) Date of Patent: Oct. 18, 2016

(54) FILLING AND IMPLANTING ACCOMMODATIVE INTRAOCULAR LENSES

(71) Applicants: Sean Caffey, Hawthorne, CA (US); Charles DeBoer, Pasadena, CA (US); Mark Humayun, Glendale, CA (US); Yu-Chong Tai, Pasadena, CA (US)

(72) Inventors: Sean Caffey, Hawthorne, CA (US); Charles DeBoer, Pasadena, CA (US); Mark Humayun, Glendale, CA (US); Yu-Chong Tai, Pasadena, CA (US)

(73) Assignee: 1Co, Inc., Pasadena, CA (US)

( * ) Notice: Subject to any disclaimer, the term of this patent is extended or adjusted under 35 U.S.C. 154(b) by 0 days.

(21) Appl. No.: 14/834,484

(22) Filed: Aug. 25, 2015

(65) Prior Publication Data
US 2015/0359626 A1    Dec. 17, 2015

Related U.S. Application Data

(63) Continuation of application No. 13/473,012, filed on May 16, 2012.

(60) Provisional application No. 61/486,562, filed on May 16, 2011.

(51) Int. Cl.
A61F 2/16        (2006.01)
A61F 9/00        (2006.01)

(52) U.S. Cl.
CPC ........... A61F 2/1662 (2013.01); A61F 2/1635 (2013.01); A61F 9/0008 (2013.01); A61F 2250/0003 (2013.01)

(58) Field of Classification Search
CPC ...... A61F 9/0008; A61F 2/1635; A61F 2/16; A61F 2/1613; A61F 2/1662; A61F 2250/0003
See application file for complete search history.

(56) References Cited

U.S. PATENT DOCUMENTS 4,822,360 A * 4/1989 Deacon ................ A61F 2/1664
                                                606/107
4,883,485 A    11/1989 Patel
4,902,293 A    2/1990 Feaster
(Continued)

FOREIGN PATENT DOCUMENTS

EP    1958592 A1    8/2008
EP    2221024 A1    8/2010
(Continued)

OTHER PUBLICATIONS

PCT International Application No. PCT/US2014/039792, Partial Search Report mailed Sep. 19, 2014, 8 pages.
(Continued)

Primary Examiner — Julie A Szpira
(74) Attorney, Agent, or Firm — Morgan, Lewis & Bockius LLP

(57) ABSTRACT

Advances in filling apparatus, handheld tools, surgical techniques and intraoperative biometry for implanting and adjusting an accommodative liquid lens are disclosed. The lens may be attached to or retained within a handheld surgical tool, which can be fluidly connectable to a filling console to fill the lens with a liquid. In various embodiments, a filling console facilitates aspirating liquid out of the lens in order to ensure the absence of residual bubbles and filling of the lens with fluid during surgery, as well as during post-operative adjustments to the lens. Actuated by the surgeon, the filling console can aspirate fluid from the lens and inject fluid into the lens following insertion thereof.

12 Claims, 5 Drawing Sheets

(56) References Cited

U.S. PATENT DOCUMENTS

| | | | |
|---|---|---|---|
| 5,554,187 A | 9/1996 | Rizzo, III | |
| 6,730,123 B1* | 5/2004 | Klopotek | A61F 2/1635 623/6.22 |
| 6,749,632 B2* | 6/2004 | Sandstedt | A61B 3/1015 623/6.22 |
| 7,438,723 B2 | 10/2008 | Esch | |
| 8,029,136 B2 | 10/2011 | Dick et al. | |
| 8,038,711 B2 | 10/2011 | Clarke | |
| 8,447,086 B2* | 5/2013 | Hildebrand | A61B 3/1173 359/290 |
| 8,603,164 B2 | 12/2013 | Peyman | |
| 2001/0049532 A1* | 12/2001 | Saishin | A61F 9/0017 606/107 |
| 2002/0055776 A1 | 5/2002 | Juan, Jr. et al. | |
| 2002/0161344 A1 | 10/2002 | Peclat et al. | |
| 2003/0083744 A1 | 5/2003 | Khoury | |
| 2004/0097957 A1 | 5/2004 | Jaker et al. | |
| 2004/0190153 A1* | 9/2004 | Esch | A61F 2/16 359/666 |
| 2006/0047339 A1 | 3/2006 | Brown | |
| 2007/0129800 A1 | 6/2007 | Cumming | |
| 2007/0142909 A1* | 6/2007 | Peyman | A61F 2/1635 623/6.11 |
| 2008/0027460 A1 | 1/2008 | Kobayashi | |
| 2008/0114372 A1* | 5/2008 | Edwards | A61M 1/0005 606/107 |
| 2008/0319451 A1* | 12/2008 | Zacharias | A61F 9/00736 606/107 |
| 2009/0240208 A1* | 9/2009 | Cowan | A61M 5/329 604/190 |
| 2011/0270596 A1 | 11/2011 | Weeber | |
| 2012/0116506 A1 | 5/2012 | Compertore | |
| 2013/0304203 A1 | 11/2013 | Beer | |
| 2013/0317607 A1 | 11/2013 | DeBoer et al. | |
| 2014/0111765 A1 | 4/2014 | DeBoer et al. | |
| 2014/0358155 A1* | 12/2014 | DeBoer | A61F 2/1662 606/107 |

FOREIGN PATENT DOCUMENTS

| | | |
|---|---|---|
| EP | 2709574 A2 | 3/2014 |
| GB | 1481427 A | 7/1977 |
| WO | 92/17132 A1 | 10/1992 |
| WO | 2004/054471 A2 | 7/2004 |
| WO | 2010/035139 A2 | 4/2010 |
| WO | 2012/067994 A2 | 5/2012 |
| WO | 2014/063135 A2 | 4/2014 |
| WO | 2014/063135 A3 | 8/2014 |
| WO | 2014/193953 A2 | 12/2014 |

OTHER PUBLICATIONS

PCT International Application No. PCT/US2013/041545, International Preliminary Report on Patentability mailed Dec. 4, 2014, 8 pages.

PCT International Application No. PCT/US2012/038102, International Preliminary Report on Patentability mailed Nov. 28, 2013, 13 pages.

PCT International Application No. PCT/US2013/041545, International Search Report mailed Aug. 19, 2013, 4 pages.

PCT International Application No. PCT/US2013/065858, International Search Report and Written Opinion mailed Jul. 2, 2014, 10 pages.

PCT International Application No. PCT/US2012/038102, International Search Report and Written Opinion mailed Nov. 30, 2012, 22 pages.

\* cited by examiner

FILLING AND IMPLANTING ACCOMMODATIVE INTRAOCULAR LENSES

RELATED APPLICATIONS

This application is a continuation of U.S. patent application Ser. No. 13/473,012, filed on May 16, 2012, which claims priority to, and the benefits of, U.S. Provisional Application Ser. No. 61/486,562, filed on May 16, 2011, the entire disclosure of which is hereby incorporated by reference.

BACKGROUND

The human eye contains a natural crystalline lens that focuses light on the retina. The lens may become cloudy, forming a cataract, which makes it impossible to see clearly. When the cataract progresses and vision becomes greatly hindered, cataract surgery becomes necessary. This procedure removes the natural lens and replaces it with an implantable medical device called an intraocular lens (IOL). The IOL is an artificial lens conventionally made of plastic, silicone, or acrylic and performs the function of a normal lens. Current IOLs are made of soft materials, allowing them to be folded and implanted in the eye with a small incision. Standard IOLs are monofocal, providing a set focal point.

IOL implantation has become the standard of care after cataract extractions. Most IOLs are made of single piece of hard material, although some newer IOLs have a two-lens design, and lenses filled with clear fluid have also been proposed. Most current IOLs are prefabricated for their lens power and then placed in the eye, but again, a few designs involve intraocular filling of the liquid in the lens at the time of initial surgery or possibly at a subsequent time (e.g., for adjustment or should the liquid become opacified, or even simply to refill the liquid in the lens). A liquid-filled bag that provides accommodation—made from, for example, an elastic, biocompatible polymer—results in numerous benefits and advantages, e.g., the ability to adjust the lens following implantation; to customize the lens to the needs of each patient; to accommodate vision; sharper vision over a wide range of distances; and reduction of visual side effects such as glares and halos. See, e.g., U.S. Pat. No. 8,038,711, the entire disclosure of which is hereby incorporated by reference.

Tailoring a fillable IOL to the ocular needs and anatomy of a particular patient requires detailed knowledge of the implantation site and the response of the lens as it is filled. Although there exist approaches to measure the overall refractive power of an eye with implantable lenses at the time of surgery (before or after IOL implantation) and also in the perioperative period, we are aware of no biometric methods for guiding the refractive power of an IOL that is filled with liquid during initial surgery or at subsequent time periods.

SUMMARY

The present invention relates to advances in filling apparatus, handheld tools, surgical techniques and intraoperative biometry for implanting and adjusting the accommodative liquid lens (ALL or simply "lens") of a liquid lens system (LLS). The ALL is implanted to replace the natural lens of an eye, interacting with the ciliary muscles, zonules, and capsule and compressing and expanding inside the eye as in normal accommodation. The LLS can also be used for presbyopia since many patients need glasses because of aging of the lens.

In broad overview, the lens may be supplied in a tightly rolled-up or compressed configuration that minimizes outer diameter and allows for a smaller surgical incision in the cornea during implantation. The lens may be attached to or retained within a handheld surgical tool, which can be fluidly connectable to a filling console to fill the ALL with a liquid such as silicone oil, hyaluronic acid (or a salt thereof, e.g., HEALON) or other fluid. In various embodiments, a filling console facilitates aspirating liquid out of the lens in order to ensure the absence of residual bubbles and filling of the lens with fluid during surgery, as well as during post-operative adjustments to the lens. Actuated by the surgeon, the filling console can aspirate fluid from the lens and inject fluid into the lens following insertion thereof. In various embodiments, the fluid used to fill the lens is supplied in a disposable (e.g., single-use) cartridge, which is snapped into the filling console for use and conveniently discharged thereafter. The cartridge may be formed of a biocompatible material.

In operation, the filling console may optionally receive signals from various sources, including optical imagery feedback; a sensor measuring the pressure inside the tip of the ALL; and/or flow or other sensors monitoring the total volume of fluid through the lens. For example, an optical calibration console (OCC) may give real-time feedback to the filling console in order to optimize clinical outcomes with respect to the amount of fluid filled inside the ALL.

Indeed, a problem with the conventional practice of filling lenses in the eye during cataract surgery is that it relies on estimates—i.e., on the surgeon's ability to fill a very small amount of fluid and estimate the amount of refraction needed. This can be very imprecise. Accordingly, embodiments of the present invention use biometry to provide feedback to the surgeon and the filling system in a closed-loop fashion to optimize filling and overall clinical outcome.

In a first aspect, the invention relates to a console for filling an accommodative liquid lens following implantation thereof. In various embodiments, the console comprises a reservoir for receiving a lens-filling fluid; a port for receiving a needle-and-tubing set; a pump for driving fluid from the reservoir to the port; and circuitry for controlling the pump to fill the lens via the needle-and-tubing set. The circuitry is responsive to signals indicative of optical imagery, ultrasound imagery, the pressure inside the lens, and/or the volume of fluid in the lens. In some implementations, the reservoir is configured to receive a disposable cartridge. Where the console's circuitry is responsive to signals indicative of the volume of fluid in the lens, the signals may be provided by a flow sensor. Where the console's circuitry is responsive to signals indicative of the pressure in the lens, the signals may be provided by a pressure sensor.

The circuitry may be responsive to optical-imagery signals provided by, for example, by an intraoperative aberrometry system (e.g., a system that performs intra-operative wavefront analysis) or another optical imaging system. Alternatively or in addition, the circuitry may be responsive to optical-imagery signals provided by an optical coherence tomography system and/or an ultrasound system.

In another aspect, the invention relates to a system for filling an accommodative liquid lens following implantation thereof. In various embodiments, the system comprises a reservoir for receiving a lens-filling fluid; a needle-and-tubing set comprising at least one of a pressure sensor or a flow sensor; a pump for driving fluid from the reservoir to the needle-and-tubing set; and circuitry for controlling the pump. The circuitry is responsive to the sensor(s) during filling.

In still another aspect, the invention relates to a method of filling an accommodative liquid lens following implantation thereof. In various embodiments, the method comprises the steps of flowing a lens-filling fluid into the lens; and automatically controlling the flow based on optical imagery, pressure inside the lens, and/or a volume of fluid in the lens. The flow may be controlled based at least in part on signals being provided by a flow sensor, a pressure sensor, and/or an intraoperative aberrometry system (e.g., performing intraoperative wavefront analysis) or other system to measure the refractive state inside the eye. The flow may be based on reducing optical aberrations and astigmatism.

In still another aspect, the invention relates to a system for filling an accommodative liquid lens following implantation thereof. In various embodiments, the system comprises a reservoir for receiving a lens-filling fluid; a needle-and-tubing set comprising a tube and a needle each having at least two separate lumens therethrough; one or more pumps for alternately driving fluid from the reservoir through one of the lumens or withdrawing fluid through the other lumen; and circuitry for operating the one or more pumps to aspirate and fill the lens via the needle. In some implementations, the lumens terminate in spaced-apart outlet ports on the needle. The system may include an air-bubble capture device (e.g., a filter or a pocket) for removing air bubbles from fluid passing through at least one of the lumens.

Yet another aspect of the invention relates to an accommodative liquid lens comprising a fillable interior portion containing (i) a fill liquid having a refractive index and (ii) a plurality of capsules containing a releasable material for altering the refractive index of the fill fluid. The capsules may be disposed within the fill liquid and/or along an interior wall of the lens. The material is releasable from the capsules upon exposure thereof to electromagnetic radiation, e.g., laser or radiofrequency radiation.

BRIEF DESCRIPTION OF THE DRAWINGS

Embodiments of the invention are better understood with reference to the following drawings. The elements of the drawings are not necessarily to scale relative to each other.

DETAILED DESCRIPTION

1. Overview

During the surgical procedure of implanting an ALL, capsulotomy and ablation of the cataract lens is performed. Capsulotomy may be performed using hand capsulorhexis techniques or using a laser (e.g., a femtosecond laser), making a small circular diameter centered on the lens or on the periphery. Phacoemulsification or laser ablation is performed and the lens is aspirated from the lens capsule. After the empty lens capsule is cleaned, the ALL is implanted and then inflated.

Before implantation into the eye, all the air from the ALL is evacuated. In one embodiment of the invention, the lens is initially filled with the appropriate filling liquid. This is done by accessing the internal contents of the lens through a refill port in the ALL, removing any air present, and then filling with the appropriate liquid. Before insertion into the eye, the ALL is evacuated entirely or almost entirely without any residual air because any residual volume is filled with the filling liquid. Typically, all air bubbles are removed as part of the assembly of the ALL.

Next, the ALL is injected into the empty lens capsule through a corneal incision and a capsulotomy. After injection into the eye, the lens is filled using the filling console. Filling the ALL completes two tasks: filling the lens to the appropriate volume, and adjusting the lens to the appropriate refractive power to provide emmetropia. The ALL must have the appropriate volume (within a clinically tolerable range) to operate properly. Proper operation includes the ability to accommodate, remain centered in the eye, adhere to the lens capsule, not damage the lens capsule, maintain an appropriate distance from the cornea and anterior chamber, and not damage surrounding tissue. For example, there is a range of volumes over which the lens capsule can transmit the appropriate force to cause the lens to accommodate. Above these volumes, the anatomical complex including the lens capsule, zonules, and ciliary muscle can no longer properly deform and accommodate the lens. In addition, an overfilled lens may damage the lens capsule and surrounding tissue or come too close to or make unwanted contact with the cornea. A underfilled lens, on the other hand, may have surface irregularities or folds that damage optical quality. Underfilling of an ALL may lower its ability to accommodate, or to conform and attach to the surrounding tissue or lens capsule, causing poor centration of the lens.

Figure 1:
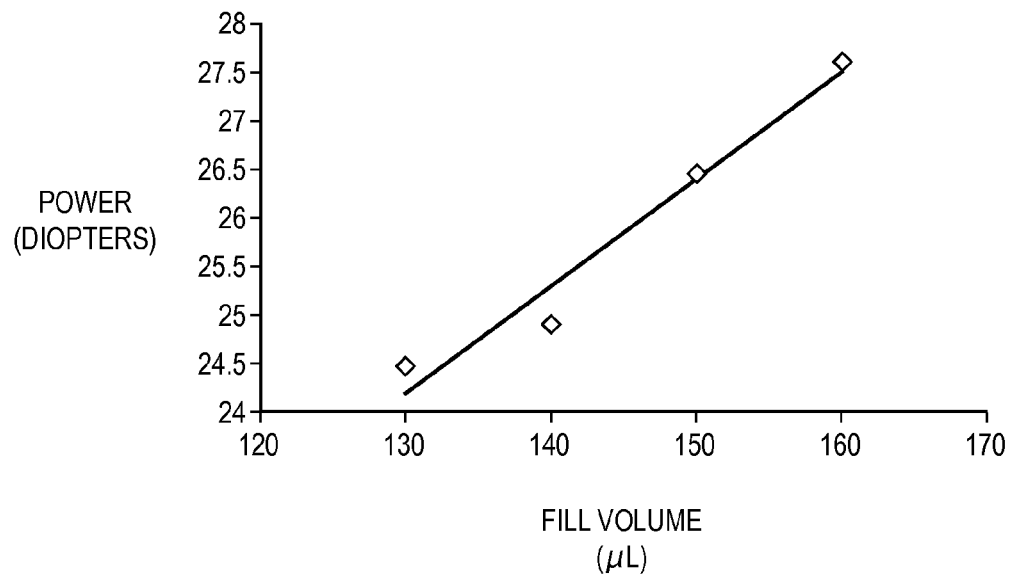
FIG. 1 graphically depicts the relationship between lens power versus fill volume of an ALL.
Figure 2:
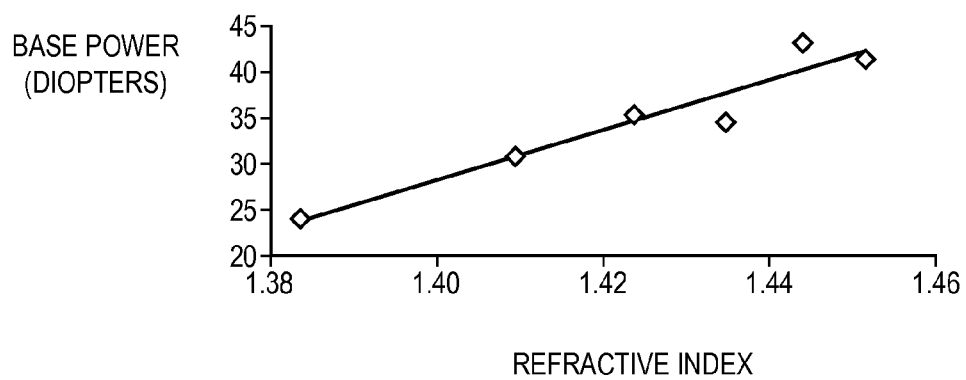
FIG. 2 graphically depicts the relationship between base Power and refractive index for an exemplary ALL.

Fill volume may be used to adjust the optical refractive power of the lens. FIG. 1 illustrates the optical power of an exemplary ALL as a function of fill volume. As fill volume is increased, optical power of the lens also increases. Therefore, the optical power of an ALL can be adjusted by adjusting its fill volume. The refractive power of an ALL can also be adjusted by changing the refractive index of filling fluid within the implant. FIG. 2 illustrates an example of modifying refractive power by adjusting the fluid refractive index for an exemplary ALL.

2. Insertion Device

Figure 3:
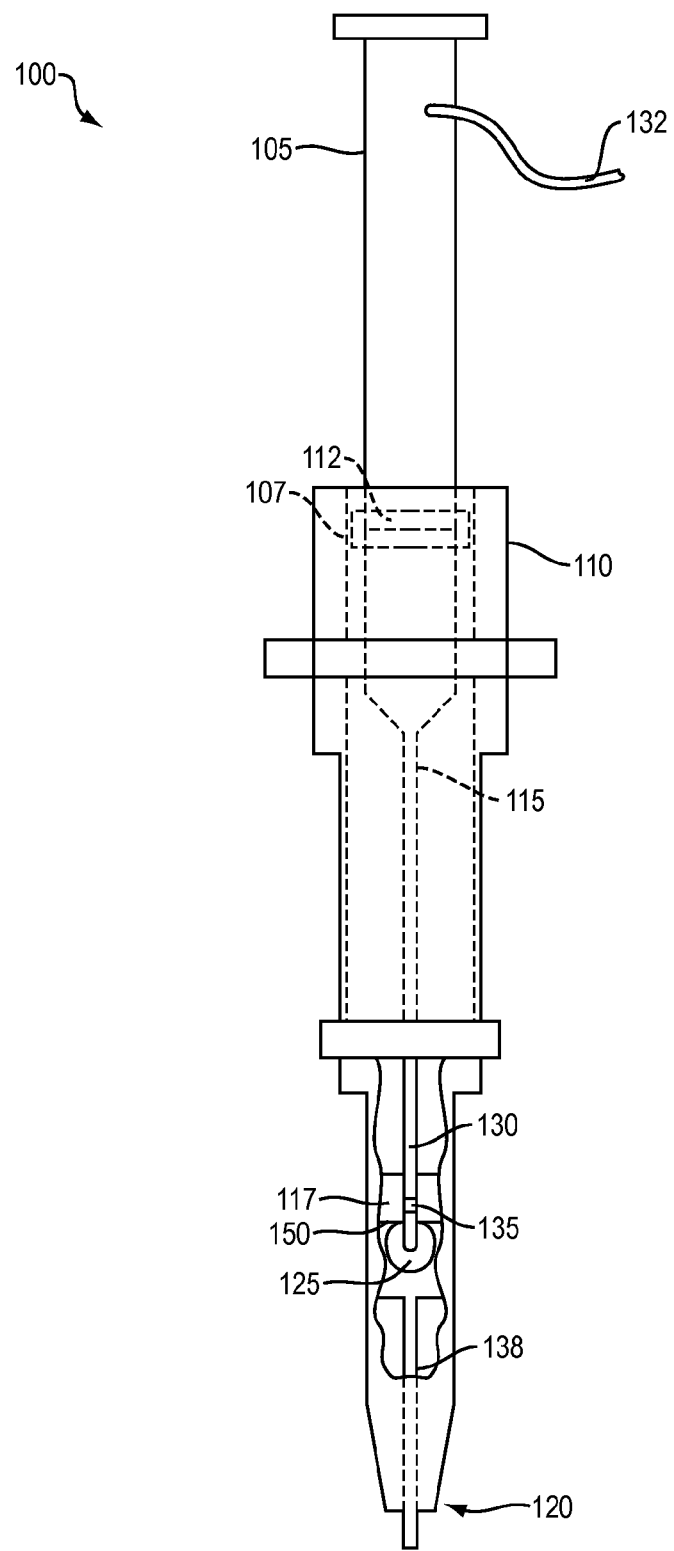
FIG. 3 is a partial-cutaway view of an insertion device in accordance herewith.

Refer now to FIG. 3, which illustrates an insertion device or "introducer" 100 that includes a hand-operated syringe-type plunger 105. The plunger 105 slides within the bore 107 of a cylindrical housing 110. Optionally, one or more O-rings 112 provide slidable frictional engagement with the interior wall of the bore 107 to facilitate smooth, controllable, hand-operated movement of the plunger 105. Projecting from plunger 105 is a smaller-diameter insertion shaft 115, which slides snugly within a plug 117 with bore 107 toward the distal end 120 of housing 110. The insertion device 100 is supplied preloaded with lens 125, which is rolled up or compressed within the bore 107. Insertion shaft 115 terminates in a filling needle 130, which, as described below, may have one or a plurality of lumens. Lens 125 resides at the end of the filling needle 130, which may project into the interior of the lens for filling thereof following implantation. Filling needle 130 is supplied by an external (multi-lumen or single-lumen) tube 132, which connects to a filling console as described below. A sensor 135, e.g., a flow sensor, a pressure sensor, or both, may be located along the length of filling needle 130 and typically at the distal end thereof. If employed, the sensor 135 is electrically connected (e.g., via wires passing through tube 132 or conductive traces thereon) to the filling console.

In operation, the surgeon makes the ocular incision and passes the distal end 120 of the insertion device 100 therethrough, maneuvering the tip until it is properly positioned within the patient's eye. Driving the plunger 105 forward causes the lens 125 to pass through the terminal bore 138 of the insertion device 100, finally being ejected into the patient's eye through the front end opening of the insertion device 100. The tip of filling needle 130 enters or remains inside the lens 125, through a resealable (and preferably self-sealing) valve, to facilitate filling thereof. Accordingly, the filling instrument provides fluidic continuity between the filling console and the internal contents of the introduced lens 125.

The filling needle 130 may have one or multiple lumens, and may interact with the lens in one or multiple positions. For simple addition or removal of fluid, the filling instrument may have a single lumen that allows fluid to be injected into or aspirated from the lens. If fluid exchange is required, e.g., to faciliate "tuning" the refractive index of the fluid by exchanging a portion of the existing fluid for a fluid with a different refractive index, a dual-lumen system is preferable. Two lumens can be used to access the same position on the lens, with one injecting fluid and the other aspirating. In addition, the lumens may access different positions in the lens 125 to allow the fluid to mix therein before the needle 130 is removed. Preferably the filling instrument interacts with a single valve, although multiple valves may be accessed if desired—e.g., to provide better mixing or filling of the ALL.

Figure 4:
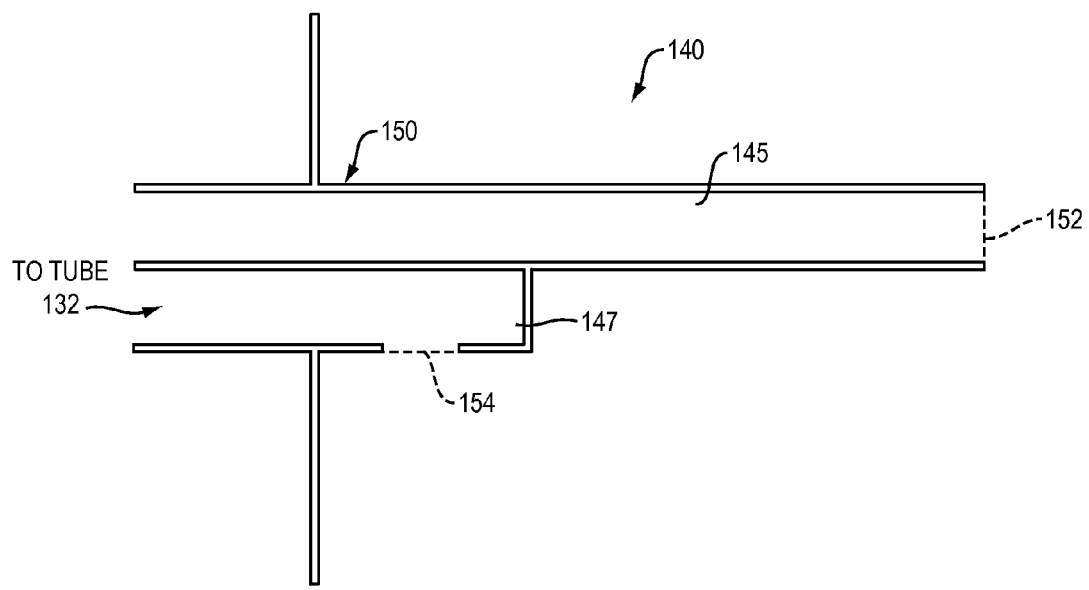
FIG. 4 is a schematic cross-section of an exemplary filling-instrument tip.

The tip 140 of a multi-lumen filling needle 130 is shown in schematically FIG. 4. The two lumens 145, 147 are in fluidic connection with complementary lumens in tube 132. One of the lumens 145, 147 may be used to infuse and the other used to aspirate fluid from the interior of lens 125. Tip 140 enters the interior of lens 125 via a re-sealable valve 150. Each of the lumens 145, 147 has an associated outlet port 152, 154, respectively. Both of these ports clear the valve 150 and reside within the interior of lens 125 during filling; they are preferentially displaced axially along the length of the tip 140 to prevent, for example, flow from the infusion port from being directly aspirated from the aspiration port. Moreover, fluid mixing within lens 125 is enhanced due to the distance between the ports 152, 154. It should be understood, however, that ports 152, 154 may both be on a single side, at the ends of the lumens, oriented in the same direction, oriented in different directions, etc. Moreover, there may be multiple ports on each lumen 145, 147. In such embodiments it is preferable to design the ports to have enough area to prevent significant fluidic resistance for the particular geometry of the instrument. Infusion and aspiration may also occur at different times to allow mixing within the lens 125.

In another embodiment, the tip 140 has a single infusion lumen terminating in a port. In this configuration fluid is either aspirated or infused through the single lumen. This has the advantage of lower flow resistance during filling because the aspiration lumen does not occupy a fraction of the total filling instrument tip diameter. However, it does not allow simultaneous infusion and aspiration.

Figure 5:
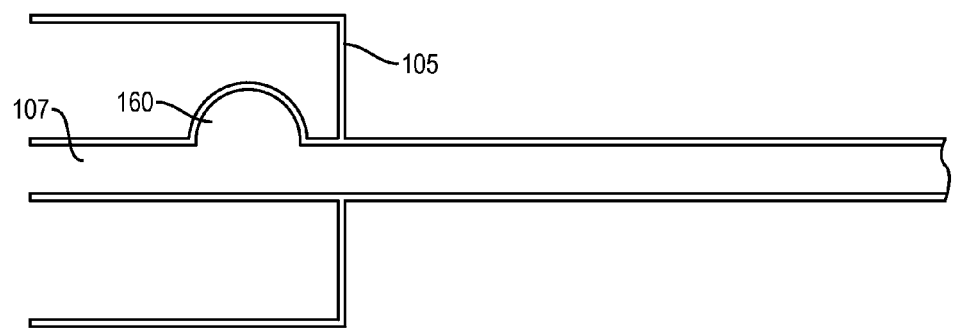
FIG. 5 is a schematic cross-section of an exemplary filling instrument with air-bubble capture within the lumen thereof.
Figure 6:
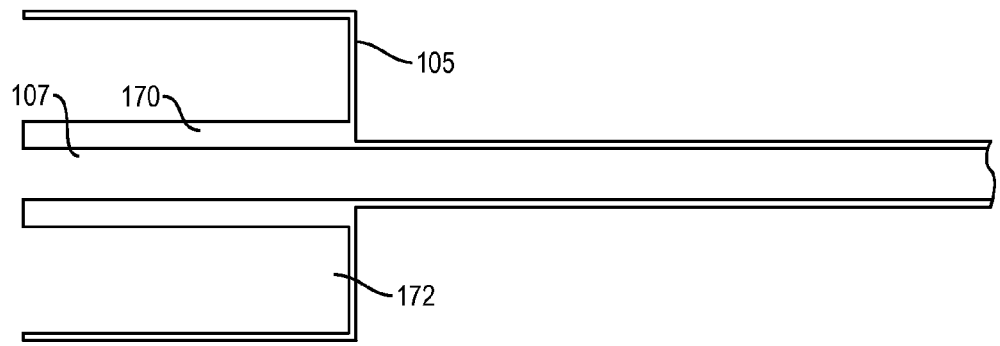
FIG. 6 is a schematic cross-section of an exemplary filling instrument with an air-bubble removal element within the lumen thereof.

If residual air bubbles are present in the lens 125 or in the line during filling, they can be removed by aspiration into the filling instrument using an air-bubble capture device or an air bubble filter. An exemplary air-bubble capture device 160 is shown in FIG. 5. The device is located within the handle or plunger of the insertion device 100. When air is aspirated through bore 160, it preferentially rises to the air-bubble capture pocket 160, where it remains, even if fluid is later infused through the bore 107. In other implementations, a maze may be used instead of the pocket 160 to entirely trap and capture the air bubble. Still another approach, shown in FIG. 6, is to use an air bubble filter 170, once again located in the handle or plunger 105. A semipermeable membrane 170 allows air but not the filling fluid to pass through it. Air bubbles in the inlet fluid line are removed as they diffuse across the semipermeable membrane 170 into a chamber 172. The chamber 172 may be subjected to vacuum conditions to help remove air bubbles.

Although the foregoing air-bubble removal mechanisms are shown in a single lumen-insertion and filling instrument, this is not meant to be limiting, and they may be used in multiple-lumen systems, such as the dual-lumen system shown in FIG. 4.

3. Filling Console

Figure 7:
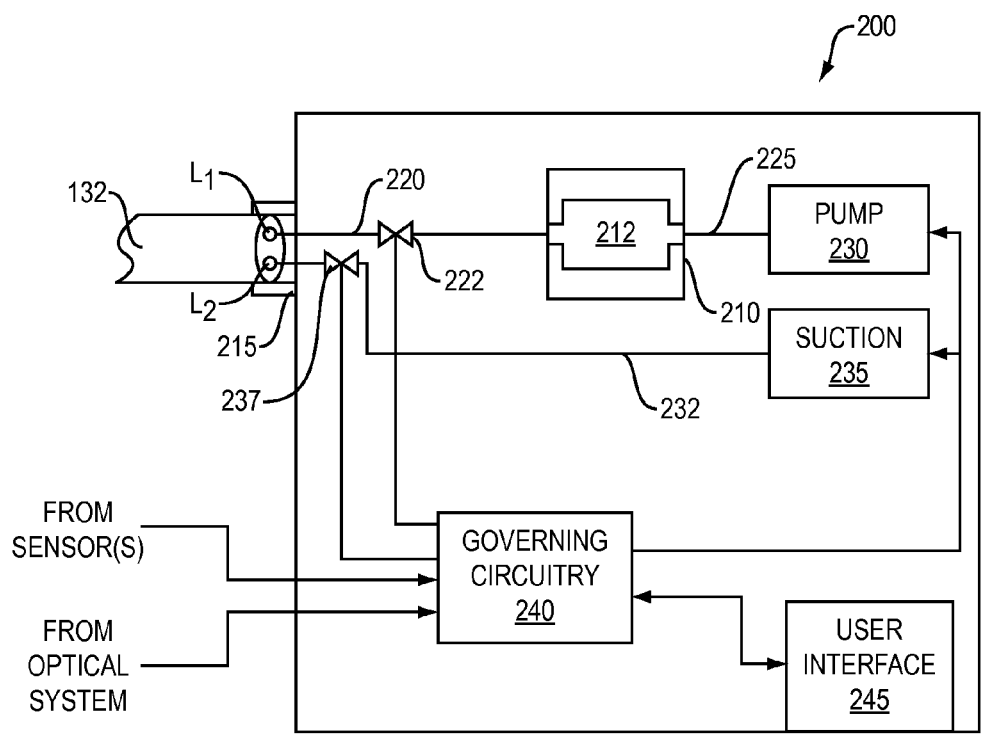
FIG. 7 illustrates a filling console operable to fill a lens inserted using, for example, the insertion device shown in FIG. 1.

The lens 125 may be filled using a filling console or unit 200, as illustrated in FIG. 7. The console 200 includes a well 210 for receiving a disposable cartridge 212, which contains the fluid that will fill the lens 125. The well 210 is configured to securely but releasably receive cartridge 212 and establish a fluid connection to the capillary network within filling unit 200, e.g., by piercing a seal on the cartridge. Typically a single-use cartridge is supplied with a single lens 125 and insertion device 100. The cartridge may include more than one fluid reservoir, e.g., to hold fluids having different refractive indices to permit the refractive index of the lens 125 to be fine-tuned by varying the proportions of the different fluids introduced therein. In other embodiments, multiple cartridges may be inserted into multiple wells 210.

The tube 132 includes two parallel (or concentric) lumens $L_1$, $L_2$. Tube 132 typically terminates in a fluid-tight connector that is releasably but securely received within a port 215 of the filling unit 200. The connector and port are mated so that the lumens of the tube 132 align with fluid channels within filling unit 200. A first fluid conduit 220 within filling unit 200 connects one end of the cartridge 212 (actually the forward port, not shown, within the well 210 that itself pierces the forward seal of and establishes fluid communication with the cartridge) to the outlet port aligned with lumen $L_1$ via a valve 222. A second fluid conduit 225 connects the opposite end of the cartridge 212 (actually the rear port, not shown, within the well 210 that pierces the rear seal of and establishes fluid communication with the cartridge) to a pump 230. The pump 230 is typically a mechanical pump (e.g., gear, diaphragm, peristaltic, pneumatic, syringe, etc.), but may also be, for example, an electrolytic pump or any other suitable pumping device. A third fluid conduit 232 connects the outlet port aligned with lumen $L_2$ to a vacuum suction 235 (i.e., an air pump) via a valve 237. (Again, in multiple-reservoir systems, the console 200 would contain multiple instances of conduits 220, 225, valve 222 and pump 230 to facilitate independent introduction of the different fluids into the lumen $L_1$.)

Valves 222, 237, pump 230 and vacuum suction 235 are controlled by governing circuitry 240, which also receives signals from sensor(s) 135 and an optical system described below. A conventional user interface 245 enables the user to program (or alter the programming of) governing circuitry 240 and to operate the filling unit 200. In some embodiments, user interface 245 includes a wireless transceiver that enables the user to program and operate the filling unit 200 using a wireless device, e.g., a "smart phone." In general, the interface will include buttons and a screen display on filling unit 200 and/or generated by governing circuitry 240 for presentation on the user's wireless device.

The control logic underlying the governing circuitry 240 may be implemented as any software program, hardware device, or combination thereof that is capable of achieving the functionality described herein. For example, the governing circuitry 240 may be an application-specific integrated circuit (ASIC) or a field programmable gate array (FPGA). Alternatively, the governing circuitry 240 may be one or more general-purpose microprocessors (e.g., any of the PENTIUM microprocessors supplied by Intel Corp.) programmed using any suitable programming language or languages (e.g., C++, C#, java, Visual Basic, LISP, BASIC, PERL, etc.). Suitable control programming is straightforwardly implemented by those of skill in the art without undue experimentation.

In basic operation, following placement of the lens 125 within the patient's eye using the insertion device 100, the surgeon activates the fill sequence via interface 245. This causes governing circuitry 240 to operate pump 230 so that fluid from cartridge 212 is driven through the (open) valve 222, through tube 132 and ultimately into lens 125 via filling needle 130. If air is present in the system, it is withdrawn by suction 235 via conduit 232 through (open) valve 237. To accommodate simultaneous fluid introduction and withdrawal, needle 130 is typically a dual-lumen needle, with each of the two lumens being fluidly coupled to the lumens $L_1$, $L_2$ of tube 132.

Governing circuitry 240 is typically programmed for careful control of the filling process so that the pressure inside the lens 125 (i.e., the fluid pressure at the outlet of the filling needle 130) does not exceed a given, critical value. The pressure may be measured by sensor 135; by governing circuitry 240 via, for example, pump 230; or by means of an external device. External monitoring devices include manual devices in mechanical contact with the lens 125 and remote monitoring systems using techniques including Brillouin scattering monitoring and acoustic/mechanical wave monitoring, such as ultrasound. In addition to controlling pressure by monitoring and adjusting the degree of filling, pressure may be controlled by supplying a desired pressure and allowing the implant to fill to that specific pressure. For example, a reservoir in fluidic continuity with the lens may be held at a given pressure, inflating the lens at that pressure until the pressures reach equilibrium.

At a minimum, pressure monitoring prevents damage to the lens 125 by overfilling, since as the volume of the lens increases, so does the pressure. The pressure inside the lens 125 may be maintained below a critical value in several ways. For example, if liquid is infused into the lens 125 pneumatically, then the governing circuitry 240 may keep injection pressure below the critical value. A pressure-release valve can also be used in the pneumatic drive as a fail-safe mechanism. As another example, if the liquid is infused using a mechanical pump 230, the pressure inside the lens 125 may be controlled by integrating a pressure sensor at the point of highest hydraulic pressure. The governing circuitry 240 may monitor the pressure sensor and employ a conventional feedback system to prevent the pressure at this point from exceeding the critical value. As still another example, the governing circuitry 240 may meter the volume of fluid delivered to the lens 125 to prevent overfilling.

In addition to preventing overfilling, monitoring pressure provides a way of indirectly monitoring the interaction between the lens and surrounding tissue to ensure a conformal fit of the lens in the lens capsule. This can be used to have the lens fit appropriately in lens capsules of differing sizes.

Governing circuitry 240 may also receive signals from an intraoperative abberometry system, described in greater detail below, that obtains three-dimensional measurements of how the lens sits within the capsule of the patient's eye and refracts the eye's light. This information may be provided to the surgeon via interface 245 to guide the filling of the lens 125, allowing the surgeon to re-shape the lens to optimize accommodation. For example, based on the observed measurements, the surgeon may operate the fill unit 200 (via user interface 245) to alter the amount of fluid within the lens 125 before withdrawing the filling needle 130 from the lens 125 (whereupon the self-sealing valve on the lens 125 reseals).

4. Monitoring

Monitoring the refractive power of the lens 125 is completed using a manual technique or using optical imagery feedback as described below. A manual technique, such as retinoscopy, can be used to determine error in the refractive power of the lens 125, and the power can be subsequently adjusted by changing the degree of lens filling. The appropriate refractive power of the lens can be set by using measurement of refractive power, choosing and filling the appropriate lens to the correct level, or it can be measured and adjusted intraoperatively. Traditionally, IOL power is measured before the surgical procedure, the correct lens is identified, and it is subsequently implanted. This is considered an open-loop technique, as there is no feedback between the lens and the filling console.

To apply the open-loop technique, the desired refractive power of the lens is determined before the surgical implantation of the device. Refractive power can be determined before the surgical operation, as is commonplace in current cataract procedures, or intraoperatively, using an intraoperative aberrometer or equivalent device. In addition, geometric measurements of the lens capsule and surrounding tissue may be taken to determine the fill volume and correct lens. Once the desired refractive power is determined, the appropriate lens is chosen along with the proper fill volume. If different fluids (e.g., fluids with differing refractive indicies) are used with the lens, the appropriate combination is also determined. Fill volume is determined by considering the refractive power desired and the geometry of the lens capsule and surrounding anatomy. After insertion into the lens capsule, the filling console operates as described previously.

The filling console can also be used in a closed-loop fashion. In closed-loop operation the refractive properties of the lens and/or eye are monitored as the lens is filled. Filling is adjusted to provide the appropriate refractive outcome as optical parameters power are monitored. In particular, the filling console (with or without the surgeon's involvement) responds to signals indicative of the relevant optical parameters, which are then used to adjust the operation of the filling pump(s). For example, the most rudimentary method of completing this task is to use intraoperative retinoscopy to check refractive error, then manually adjust the lens accordingly and re-check. Preferably the refractive power of the lens is monitored throughout the procedure in an automated manner while the lens is filled. Using the filling console in closed-loop operation yields refractive outcomes that are less prone to error than prior techniques. This is because the actual power is monitored and adjusted in real-time. Open-loop techniques, by contrast, rely solely on data obtained before implantation, and cannot adjust for changes based on the procedure, or errors in the refractive calculations.

Optical imagery feedback—i.e., measurements indicating the optical positioning and performance of the implanted lens—may be used in closed-loop implementations to help the surgeon guide the lens and determine the proper level of lens filling. Suitable instruments include an aberrometer, a refractometer, or an imaging system to monitor geometry and calculate power, such as an optical coherence tomography system, or an ultrasound system. In addition, this instrument may use prior biometry measurements in conjunction with measurements during the filling of the lens 125. For example, to determine appropriate power, an optical coherence tomography system may be used to monitor the lens profile in conjunction with information previously collected regarding the length of the eye, or refractive power of the cornea. Using prior information the lens geometry is adjusted to the refractive power and/or geometry.

Figure 8:
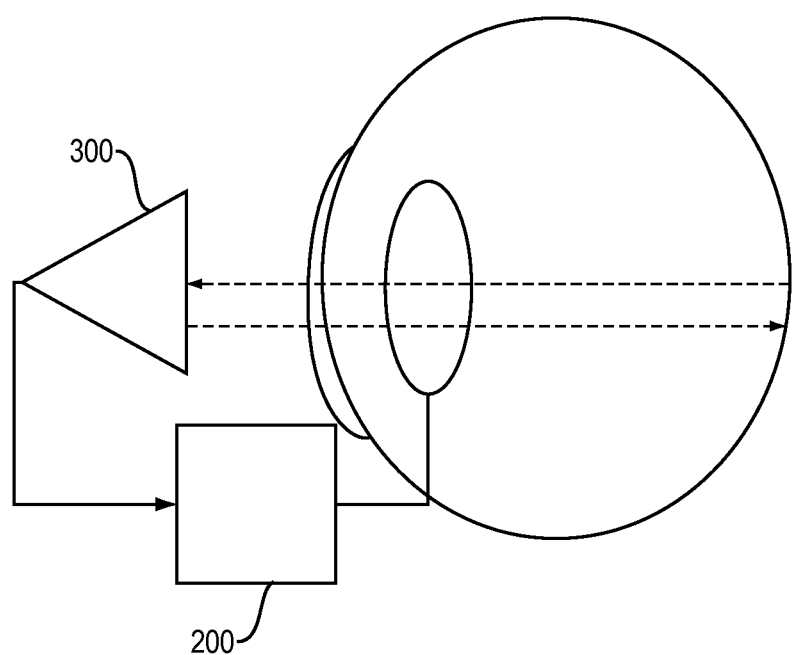
FIG. 8 shows a system for providing intraoperative wavefront abberometry in order to facilitate proper positioning and/or filling of the lens.

In one embodiment, an intraoperative aberrometry system that obtains three-dimensional measurements of how the lens sits within the capsule and refracts the eye's light is employed, and the information obtained may be provided to the surgeon to guide the filling of the lens, allowing the surgeon to re-shape the lens to optimize refractive power, reduce or eliminate optical aberrations, and optimize accommodation. Using a measurement system that performs intraoperative wavefront analysis, for example, enables extremely precise, individualized vision-correction outcomes to be achieved—outcomes that would be impossible with traditional surgeon's perspective in filling the lens 125. With reference to FIG. 8, a conventional intra-operative wavefront analysis system 300 includes a coherent light source, a beam-modification device for shaping and deflecting a beam of the coherent light source that is directed through the patient's eye to the retina, and a wavefront analyzer for receiving reflected light from the retina and analyzing a wavefront of the optical path in the eye. The wavefront analyzer may be based on a Shack-Hartmann sensor, for example. See, e.g., U.S. Pat. No. 8,029,136, the entire disclosure of which is hereby incorporated by reference; a suitable commercially available system 300 is the ORA system supplied by WaveTec Vision, Aliso Viejo, Calif. In some embodiments the output of the wavefront analysis is used directly by the filling console 200 in an automated feedback loop, e.g., to provide an automated fill and/or to stop a manual filling operation when clinical safety margins are approached. Ultrasound or optical coherence tomography can be used in a similar manner to calculate the optimal refraction of the lens and therefore give feedback on how much the lens should be filled.

The output of the wavefront analysis is provided to the governing circuitry 240 of the filling unit 200. In some embodiments, governing circuitry 240 uses signals from the system 300 in an automated feedback loop, e.g., to provide an automated fill and/or to stop a manual filling operation when clinical safety margins are approached. In addition, optical information may be provided to the surgeon via user interface 245 to enable the surgeon to observe the optical performance of the introduced lens and alter the fill level and/or positioning to beneficially alter the performance.

Ultrasound can be used in a similar manner to calculate the optimal refraction of the lens and therefore give feedback on how much the lens 125 should be filled. Commercial systems such as the Zeiss IOLMaster 500 can be used to determine the appropriate orientation of the lens 125 as well as to screen the eye before and during surgery to make sure the correct size and refractive-strength lens is chosen. Ultrasound systems provide axial length and keratometry measurements as well as IOL power calculation, which varies with the level of lens filling. Ultrasound measurements along the visual axis can be used to ensure proper lens placement in terms of axial distance.

The filling console 200, or a separate filling unit, may be used to refill the lens to re-adjust for post-surgical changes in accommodation and refraction. The filling console 200 is connected to a disposable tubing set with a small-gauge needle to pierce the cornea and enter the chamber of the lens 125. Post-implantation assessment and refilling takes place after the eye has had time to heal and the lens has had time to settle—e.g., the day after surgery. The goal of this step is to make adjustments to optimize the patient's vision towards normal. The clinician may refill the lens 125 multiple times after surgery to achieve optimal vision.

The approach of the present invention may also be used to monitor and adjust for astigmatism. Certain configurations of the lens 125 have the ability to correct for astigmatism. Therefore, astigmatism and other aberrations can be monitored and corrected for during the surgical procedure. This can also be used when placing non-liquid lens such as Toric IOLs. For example, after a monofocal toric IOL is placed, the correct angular position can be determined with the optical system while the surgeon adjusts the position during the procedure.

In certain embodiments of the invention, the filling system is used with a non-invasive lens-tuning mechanism. Release capsules in the lens fill fluid may include a high concentration of solutes, nanoparticles, or a refractive fluid. Upon opening of the capsules by means of targeted laser ablation or actuation with radiofrequency exposure, the contents of the affected capsules are released into the lens fill fluid, thereby adjusting refractive power of the lens. Alternatively, the release capsules may be implanted along the interior wall of the lens. In a postoperative setting, the lens refractive power can be monitored with an optical instrument as described above as the release capsules are progressively opened. Upon reaching emmetropia, the procedure is completed.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for filling an accommodative liquid lens following implantation thereof, the system comprising:
   a reservoir for receiving a lens-filling fluid;
   a needle-and-tubing set comprising a tube and a needle having at least one lumen therethrough and an outlet port associated therewith;
   one or more pumps for alternately driving or withdrawing fluid from the reservoir through at least one said lumen;
   circuitry for operating the one or more pumps to aspirate and fill the lens via the needle; and
   an air-bubble capture device comprising a maze for removing air bubbles from fluid passing through at least one said lumen prior to exiting the needle into the lens through one of the outlet ports.

2. The system of claim 1 wherein the needle has a plurality of lumens that terminate in spaced-apart outlet ports on the needle.

3. The system of claim 1 wherein the capture device further comprises a filter.

4. The system of claim 1, wherein the air-bubble capture device is located at a proximal end of the needle.

5. The system of claim 1, further comprising a handle, the air-bubble capture device being located within the handle.

6. A system for filling an accommodative liquid lens following implantation thereof, the system comprising:
   a reservoir for receiving a lens-filling fluid;
   a needle-and-tubing set comprising a tube and a needle having at least one lumen therethrough and an outlet port associated therewith;
   one or more pumps for alternately driving or withdrawing fluid from the reservoir through at least one said lumen;
   circuitry for operating the one or more pumps to aspirate and fill the lens via the needle; and
   an air-bubble capture device for removing air bubbles from fluid passing through at least one said lumen prior to exiting the needle into the lens through one of the outlet ports,
   wherein the air-bubble capture device comprises a semi-permeable membrane allowing air but not the fluid to pass therethrough.

7. The system of claim 6, wherein the air-bubble capture device further comprises an air-bubble capture pocket.

8. The system of claim 6, further comprising a vacuum mechanism interfacing with the semipermeable membrane to facilitate the removal of air bubbles.

9. The system of claim 6, wherein the needle has a plurality of lumens that terminate in spaced-apart outlet ports on the needle.

10. The system of claim 6, wherein the capture device further comprises a filter.

11. The system of claim 6, wherein the air-bubble capture device is located at a proximal end of the needle.

12. The system of claim 6, further comprising a handle, the air-bubble capture device being located within the handle.

* * * * *